United States Patent [19]

Adams et al.

[11] 4,048,332

[45] Sept. 13, 1977

[54] PHENYLALKANOIC ACIDS

[75] Inventors: Stewart S. Adams; Bernard J. Armitage; John S. Nicholson, all of Nottingham, England

[73] Assignee: The Boots Company Limited, Nottingham, England

[21] Appl. No.: 656,220

[22] Filed: Feb. 9, 1976

Related U.S. Application Data

[63] Continuation-in-part of Ser. No. 367,614, June 6, 1973, Pat. No. 3,969,402.

[51] Int. Cl.$^2$ ............... A61K 31/05; A61K 31/19; A61K 31/42; A61K 31/165
[52] U.S. Cl. ............... 424/317; 424/272; 424/308; 424/324; 424/346
[58] Field of Search ............... 424/317, 272, 308

[56] References Cited

U.S. PATENT DOCUMENTS

| 3,624,142 | 11/1971 | Shen et al. | 260/473 R |
|---|---|---|---|
| 3,671,580 | 6/1972 | Shen et al. | 260/473 S |

FOREIGN PATENT DOCUMENTS 1,091,403  11/1967  United Kingdom ............... 260/473

*Primary Examiner*—Stanley J. Friedman
*Attorney, Agent, or Firm*—Lawrence Rosen; E. Janet Berry

[57] ABSTRACT

Therapeutic compositions comprising 2-(hydroxy-substituted-4-biphenylyl)propionic acids and methods of treatment of inflammation, pain, fever and preventing blood platelet aggregation with these compounds.

23 Claims, No Drawings

PHENYLALKANOIC ACIDS

This application is a continuation in part of our application Ser. No. 367,614 filed June 6, 1973 now U.S. Pat. No. 3,969,402.

This invention relates to novel substituted propionic acids and derivatives thereof which have been found to possess valuable biological properties According to the invention there is provided a therapeutic composition useful in the treatment of pain, inflammation, pyretic conditions or in inhibiting blood platelet aggregation which comprises a compound of formula I

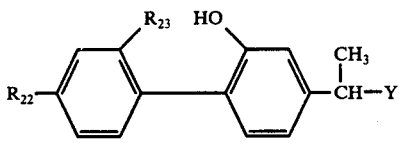

wherein $R_{22}$ and $R_{23}$ are selected from hydrogen and halogen and y is COOH, CONH$_2$, CH$_2$OH, CONHOH or

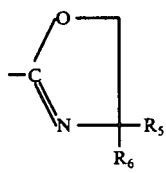

wherein $R_5$ and $R_6$ are the same or different alkyl or hydroxyalkyl, or a pharmaceutically acceptable ester (i.e. compounds wherein Y is COOR$_4$ in which R$_4$ is an esterifying radical) or a pharmaceutically acceptable salt of a compound wherein Y is COOH, in association with a pharmaceutical excipient. R$_4$ is usually C$_{1-4}$ alkyl. The term "halogen" designates chlorine, bromine or fluorine.

The compounds of general formula I possess antiinflammatory activity and are useful for the treatment of inflammatory conditions. They also possess analgesic and antipyretic properties and are useful for the treatment of conditions of pain and pyretic conditions. Their activity has been determined in experimental animals using pharmacological tests which are known to be capable of characterising compounds possessing the therapeutic properties of aspirin, namely anti-inflammatory, analgesic and antipyretic activity.

The therapeutic activity of the compounds in assessed in various ways. For example the anti-inflammatory activity is determined in the test described by Adams and Cobb, Nature 1958, 181, 733. The activity of the test compounds is compared with that of aspirin against ultra-violet light induced erythema on the depilated skin of guinea pigs.

Another way of determining anti-inflammatory activity is by rat adjuvant arthritis test in which an arthritis is produced by injecting intradermally into the tail 0.1 ml. of a suspension of killed human tubercle bacilli (6 mg./ml.) in liquid paraffin BP. A polyarthritis develops over the next 3 weeks in untreated controls. The compounds under test (vehicle only for control animals) are given daily by mouth from the day the adjuvant is injected for 21 days. On day 21 the degree of arthritis is assessed on each hind foot. The degree of inhibition produced by a compound is estimated by comparison of the total arthritic scores with those found in the controls.

The analgesic activity of the compounds is determined in the rat using a modification of the technique described by Randall and Selitto, Arch. int. Pharmacodyn, 1957, 111, 409. In this technique the analgesic effect of the drugs is compared with aspirin by determining the increase in pain threshold when pressure is applied to the inflamed foot.

The anti-pyretic effect is determined in rats in which the body temperature has been raised by a subcutaneous injection of a yeast suspension. Comparison of the compounds under test is made with graded doses of aspirin.

Preferred compounds of the invention are those wherein Y is COOH. It is believed that when salts, esters, the amide, the hydroxamic acid, the oxazoline or the alcohol derived from the acid are used in place of the acid, said derivatives are metabolised by the animal body and are converted in the body into the corresponding acid. Preferably the halogen is selected from chlorine and fluorine. An interesting group of compounds are those in which $R_{22}$ is halogen, especially fluorine or chlorine. Another interesting group of compounds are those in which $R_{23}$ is hydrogen.

It will be appreciated that, since the compounds of general formula I possess an asymmetric carbon atom, they are ordinarily present in the form of a racemic mixture. The resolution of such racemates may be carried out by any conventional method and the separated optically active stereoisomers form part of the present invention.

The compounds of the invention may be administered in the conventional manner of aspirin or usual manner for other anti-inflammatory, analgesic, and antipyretic agents, for example orally, topically, rectally or parenterally, preferably orally. The optimum dosage rate varies with the route of administration, but normally lies within the range 0.03 – 60 mg./kg./day, more usually between 0.70 – 30 mg./kg./day. The unit dose may vary from 1 mg. to 1000 mg. per subject; for oral administration the dosage rate is preferably 2 – 2000 mg. per subject per day, optionally in divided doses.

In use, the compounds of the invention are administered in conventional formulations and accordingly the invention also provides thereapeutic compositions which comprise, as an active ingredient, a compound of the invention together with a pharmaceutically acceptable carrier. Pharmaceutically acceptable carriers suitable for the production of compositions for oral, topical, rectal or parenteral administration are well known in the art. The compositions of the invention suitably contain 0.1 – 90% by weight of a compound of the invention.

Compositions for oral administration are the preferred compositions of the invention, and these are the conventional pharmaceutical forms for such administration, such as for example tablets, capsules, lozenges, powders, effervescent granules, syrups and aqueous and oily suspensions. The excipients used in the preparation of these compositions are the excipients of the pharmacist's art. Thus in the preparation of tablets, typical excipients include disintegrating agents, for example maize starch and lubricating agents such as magnesium stearate; in the preparation of capsules, standard gelatin capsules may be used containing the active ingredient alone or admixed with a diluent. The liquid compositions may comprise as excipients water and sucrose to provide syrups, water, dispersing agents and suspending agents, for example sodium carboxymethylcellulose to provide aqueous suspensions, and a non-toxic oil, for example a vegetable oil such as arachis oil and a suspending agent to provide oily suspensions.

Compositions for rectal administration are the conventional pharmaceutical forms for such administration, such as for example suppositories with cocoa butter or polyethylene glycol bases.

Compositions for topical use are the conventional pharmaceutical forms for such application, such as ointments, creams and lotions. Ointments and creams may be water miscible or water-immiscible in character and include emulsions prepared from emulsifying waxes and oils and those prepared from water miscible polyethylene glycols. Lotions may comprise a solution in an aliphatic alcohol with 1 - 4 carbon atoms which may contain a small proportion of water.

Compositions for parenteral administration are the conventional pharmaceutical forms for such administration, for example sterile suspensions in aqueous or oily media or sterile solutions in propylene glycol.

In some formulations it may be beneficial to use the compounds of the invention in the form of particles of very small size, such as for example, as obtained by fluid energy milling, for example micronizing.

The invention further provides a method of treating inflammatory conditions, conditions of pain and pyretic conditions, individually or in any combination, in warmblooded animals including man, which comprises administering a compound of the invention, preferably orally.

The products of the present invention may of course be employed in combination with other active anti-inflammatory agents, analgesics, and antipyretic agents, or with other drugs, as is already conventional in the art for other existing anti-inflammatory, analgesic and antipyretic materials such as aspirin.

The compounds of the invention have other valuable properties. For example, they possess fibrinolytic and thrombolytic activity and also inhibit platelet agregation induced by various agents such as adrenaline.

The fibrinolytic activity is assessed by the euglobulin lysistime test described by Van Kaulla in Chemistry of Thrombolysis: Human Fibrinolytic Enzyme, 1963, p79, published by Charles C. Thomas, Springfield, Illinois.

The thrombolytic activity is assessed by the hanging clot test described by Van Kaulla, *J. Med. Chem.* 1965, 8, 164.

The effect on platelet aggregation is assessed by the test of Born; *Nature*, 1962, 194, 927.

Drugs possessing such properties are useful in the treatment and/or prophylazis of various thrombotic disorders. When being used in such treatment or prophylaxis they may be formulated and administered in a manner similar to that when being used as anti-inflammatory agents, as described previously.

The compounds of the invention may be prepared by removing any phenolic protecting group X from a compound of the general formula II

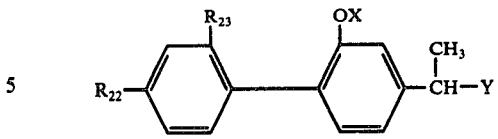

Phenolic protecting groups X are well known in the art and include, for example, lower alkyl (perferably methyl), benzyl and tetrahydropyranyl. Thus, for example, a lower alkoxy (preferably methoxy) or benzyloxy group may be converted to hydroxy by dealkylation (preferably demethylation) or debenzylation, which may be effected, for example, by heating with HBr in a suitable solvent such as aqueous acetic acid. As another example, benzyloxy may be converted to hydroxy by hydrogenolysis. Such hydrogenolysis may be carried out in a conventional manner, for example by reaction with hydrogen at atmospheric pressure or above in the presence of a suitable catalyst, for example palladium on charcoal or platinum oxide. As a further example, a tetrahydropyranyloxy group may be converted to hydroxy in a conventional manner, for example by reaction with a suitable acid, for example a mineral acid, in a suitable aqueous solvent.

The intermediate compounds of general formula II may be prepared by methods analogous to those described in our British patent specification No. 1,091,403 and Belgian patent specifications Nos. 764257 and 764258.

Further typical methods for the preparation of the compounds of the invention are as follows. Processes for the preparation of the stated starting materials and exact reaction conditions for the typical methods described will be readily apparent to those skilled in the art and, further, typical methods for the preparation of starting materials are given in some of the examples. In the following description for the preparation of the acids and the various acid derivatives the symbol $R_o$ has been used to represent the radical

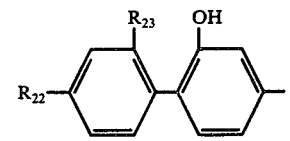

Decarboxylation of a compound of formula III

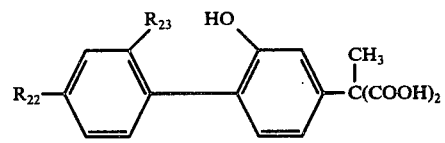

wherein $R_{22}$ and $R_{23}$ are hydrogen or halogen. The decarboxylation reaction may be effected by heating compound III at a suitable temperature, for example 180°–220° C. Compound III may be prepared from 2-phenyl-o-quinol acetate (Wesseley et al., *Monatsh.* 1952, 83, 1260) as follows:

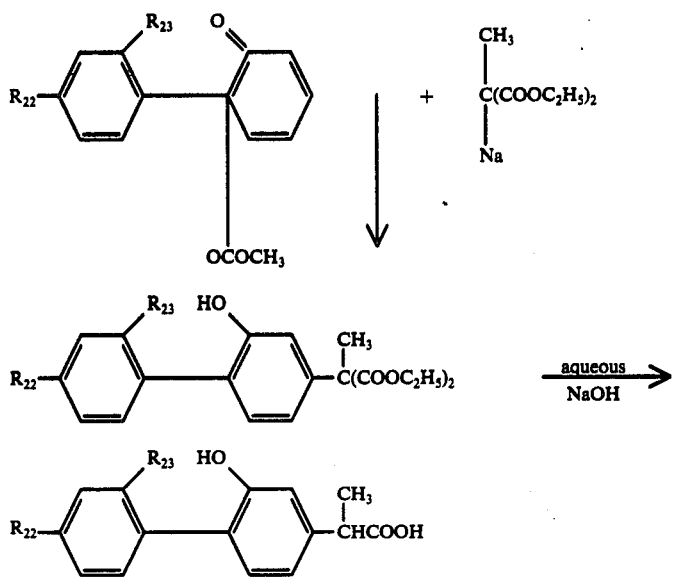

Esters

1. Esterification of the acids by conventional means, for example:

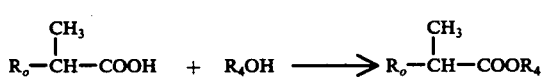

or

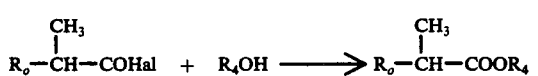

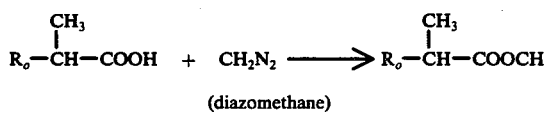

(diazomethane)

Amides

Preparation of the amides by conventional means, for example:

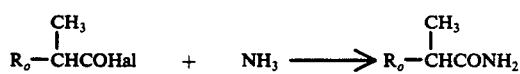

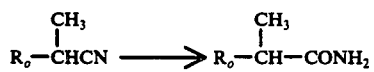

Salts

1. Reaction of the acids with organic or inorganic bases. Typical inorganic salts that may be formed are the sodium and potassium salts. Typical organic salts that may be formed are amine salts, including hydroxy amine salts. For example salts with triethylamine or diethylaminoethanol or benzylamine may be formed.

Alcohols

1. Reduction of the acids or, preferably, the esters (especially alkyl esters). The use of lithium aluminium hydride in a suitable solvent for example ether, followed by acidification, is one example. Alternatively hydrogenation in the presence of a copper/chromium oxide catalyst may be used. Esters may be reduced with sodium in a lower alkanol.

Oxazolines

1. Preparations from the acids by conventional means, for example:

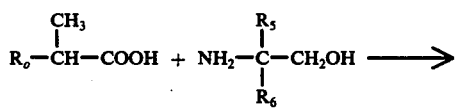

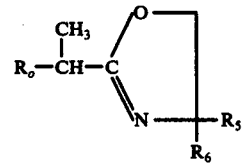

Hydroxamic Acid

Preparation by conventional means: e.g.

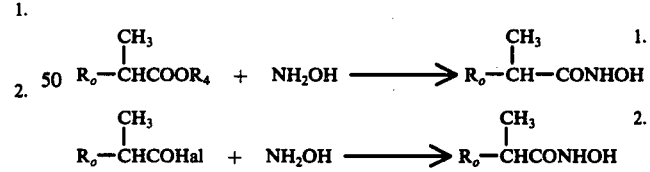

The invention is illustrated in the following examples in which "parts" and "percentages" are by weight unless otherwise stated. In the Examples the term "ether" denotes diethyl ether.

EXAMPLE 1

4-fluoroiodobenzene and 4-bromo-3-nitroacetophenone were reacted under Ullmann conditions to give 4-acetyl-4'-fluoro-2-nitrobiphenyl, m.p. 88°–90° C. (from methanol). This compound was reduced with stannous chloride in concentrated hydrochloric acid to give 4-acetyl-2-amino-4'-fluorobiphenyl, m.p. 88°–91° C. (from methanol). The amino group in this compound was converted to methoxy in the following way:

A solution of sodium nitrite (12.0 g.) in water (40 ml.) was added to a stirred solution of 4-acetyl-2-amino-4'-fluoro-biphenyl, (36.6 g.) in 5N sulphuric acid (480 ml.), whilst maintaining the temperature of the reaction mixture at 0°–5° C. The reaction mixture was stirred at 0°–5° C. for a further 1 hour. The resulting cold solution of diazonium salt was poured slowly into stirred refluxing 5N sulphuric acid (400 ml.). When the addition was complete, refluxing was continued for 0.5 hour. The resulting solution was poured into ice/water, causing the precipitation of a solid which was collected, dried and dissolved in ether. The ethereal solution was extracted with dilute aqueous sodium hydroxide and the extract was acidified to precipitate a product which was extracted into ether. The ethereal extract was washed with water, dried over anhydrous sodium sulphate, and evaporated to give a product which was recrystallized from light petroleum (b.p. 80°–100° C.) to give the novel intermediate 4-acetyl-4'-fluoro-2-hydroxybiphenyl, m.p. 152°–154° C. A mixture of this compound (36.5 g.), dimethyl sulphate (25.2 g.) and potassium carbonate (25 g.) in anhydrous acetone (200 ml.) was refluxed with stirring overnight. Acetone was removed by evaporation, the residue poured into water, and the resulting mixture extracted with ether. The ether extract was washed with dilute sodium hydroxide solution, then with water and dried over anhydrous sodium sulphate. Ether was removed by evaporation and the residue was distilled in vacuo to give a product, b.p. 142°–144° C./0.2 mm. which solidified on cooling. This solid was recrystallized from light petroleum (b.p. 62°–68° C.) to give the novel intermediate 4-acetyl-4'-fluoro-2-methoxybiphenyl, m.p. 75°–77° C.

This was then subjected to a Darzens synthesis using sodium isopropoxide and ethyl chloroacetate and the crude glycidic ester obtained was treated by first sodium hydroxide and then sodium metabisulphite to give 2-(4'-fluoro-2-methoxy-4-biphenylyl)propionaldehyde, b.p. 144°–146° C./0.3 mm. This was treated with hydroxylamine sulphate and sodium acetate to give the oxime which was collected and then treated with aqueous nickel sulphate. The mixture was heated to reflux and aqueous sodium hydroxide added, and reflux continued for 24 hours. The mixture was acidified extracted with ether, the ether extracts extracted with aqueous potassium carbonate, these extracts were acidified and re-extracted with ether, dried and evaporated to give 2-(4'-fluoro-2-methoxy-4-biphenylyl)propionic acid, m.p. 133°–136° C. (from light petroleum, b.p. 100°–120° C.).

A solution of 2-(4'-fluoro-2-methoxy-4-biphenylyl)-propionic acid (10 g.) in a mixture of hydrobromic acid (270 ml. of 48%w/v aqueous acid) and glacial acetic acid (90 ml.) was refluxed for 3.5 hours. The resulting solution was poured onto crushed ice, causing the precipitation of a solid product. This product was collected by filtration, washed with water, dried and recrystallised from chloroform/light petroleum (b.p. 62°–68° C.) to give 2-(4'-fluoro-2-hydroxy-4-biphenylyl)-propionic acid, m.p. 138°–142° C.

EXAMPLE 2

4-Chloroiodobenzene and 4-bromo-3-nitroacetophenone were reacted under Ullmann conditions to give the novel intermediate 4-acetyl-4'-chloro-2-nitrobiphenyl, m.p. 103°–105° C. (from methanol). This compound was reduced with stannous chloride and concentrated hydrochloric acid to give 4-acetyl-2-amino-4'-chlorobiphenyl, m.p. 139°–140° C. (from methanol). This compound was converted to the novel intermediate 4-acetyl-4'-chloro-2-hydroxybiphenyl and thence to the novel intermediate 4-acetyl-4'-chloro-2-methoxybiphenyl, b.p. 167°–170° C./0.4 mm., by diazotization and methylation methods analogous to those described in Example 1.

By methods analogous to those described in Example 1, 4-acetyl-4'-chloro-2-methoxybiphenyl was converted to the novel intermediate 2-(4'-chloro-2-methoxy-4-biphenylyl) propionaldehyde, b.p. 174°–175° C./0.7 mm. (solidified on cooling) and thence to the novel intermediate 2-(4'-chloro-2-methoxy-4-biphenylyl)propionic acid, m.p. 127°–128° C. (from light petroleum, b.p. 80°–100° C.)

This was converted to 2-(4'-chloro-2-hydroxy-4-biphenylyl)propionic acid, m.p. 134°–135° C. (from light petroleum, b.p. 80°–100° C.) by reaction with hydrobromic acid in acetic acid in an analogous manner to that described in Example 1.

EXAMPLE 3

To a stirred mixture of sodium (0.97 g.) in absolute ethanol (30 ml.) was added diethyl methylmalonate (9.2 ml.) followed by the addition of a solution of 2-phenyl-o-quinol acetate (9.8 g.) in warm absolute ethanol (120 ml.). The mixture was refluxed with stirring for 3.5 hours, and then ethanol was removed by evaporation under reduced pressure. To the residue was added 2.5N aqueous sodium hydroxide (78 ml.) and the mixture refluxed for 1.5 hours. The resulting solution was cooled and acidified to precipitate a product which was collected by filtration, washed with water, and dried in vacuo to give the novel intermediate 2-(2-hydroxy-4-biphenylyl)-2-methylmalonic acid. This compound was heated at 200° C. for 20 minutes to give a product which was recrystallised from benzene and then light petroleum, b.p. 80°–100° C., to give 2-(2-hydroxy-4-biphenylyl)propionic acid, m.p. 120°–124° C.

EXAMPLE 4

By methods analogous to those described in Example 1, 4-acetyl-2-amino-2',4'-difluorobiphenyl was converted to the novel intermediate 4-acetyl-2',4'-difluoro-2-hydroxybiphenyl, m.p. 171°–173° C. (from industrial methylated spirits), and thence to the novel intermediate, 4-acetyl-2',4'-difluoro-2-methoxybiphenyl, m.p. 89°–91° C. (from light petroleum b.p. 62°–68° C.).

This was then converted to crude 2-(2',4'-difluoro-2-methoxy-4-biphenylyl)propionaldehyde and thence to the novel intermediate 2-(2',4'-difluoro-2-methoxy- 4-biphenylyl)propionic acid, m.p. 148°–149° C. (from methylene chloride/light petroleum, b.p. 62°–68° C.).

This was then converted to 2-(2',4'-difluoro-2-hydroxy-4-biphenylyl)propionic acid, m.p. 138°–140° C. (from chloroform) by reaction with hydrobromic acid in acetic acid.

EXAMPLE 5

2(2-Fluoro-4-biphenylyl)propionic acid (1 g.) ethylene glycol (10 ml.) and potassium hydroxide (0.8 g.) were refluxed under nitrogen for 24 hours. The mixture was diluted with water, washed with ether, acidified with hydrochloric acid and extracted with ether. The ether extract was washed with water, dried and evaporated to dryness. The product was subjected to thin layer chromatography to give 2-(2-hydroxy-4-biphenylyl)propionic acid, which was recrystallised from light petroleum (b.p. 80°-100° C.) to give the purified acid having a m.p. of 112°-119° C.

EXAMPLE 6

An ethereal solution of 2-(2-hydroxy-4-biphenylyl)-propionic acid was treated with excess diazomethane and the resulting mixture evaporated to dryness under reduced pressure. The resulting product was triturated with light petroleum, b.p. 40°-60° C., collected by filtration and dried. The product was recrystallised twice from light petroleum (b.p. 80°-100° C.) to give methyl 2-(2-hydroxy-4-biphenylyl)propionate, m.p. 105.5°-107.5° C.

EXAMPLE 7

A solution of 2-(2',4'-difluoro-2-hydroxy-4-biphenylyl)propionic acid (4.5 g.) in absolute ethanol (50 ml.) containing concentrated sulphuric acid (2 ml.) was refluxed overnight (16 hours). After distillation of ethanol the residue was poured onto ice-water and the product was isolated in ether. The extracts were washed with dilute sodium bicarbonate dried and evaporated. The solid residue thus obtained was purified by two crystallisations from light petrol (b.p. 62°-68° C.), to give ethyl 2-(2',4'-difluoro-2-hydroxy-4-biphenylyl)-propionate, m.p. 72°-73° C.

EXAMPLE 8

A solution of ethyl 2-(2',4'-difluoro-2-hydroxy-4-biphenylyl)propionate (2.0 g.), from the previous Example, in dry ether (40 ml.) was added over 15 minutes in dry ether (40 ml.). After stirring under reflux for 1.5 hours, excess lithium aluminium hydride was decomposed by the cautious addition of water and finally with 2N sulphuric acid (10 ml.). The product was isolated in ether, washed, dried, evaporated and distilled to give a thick translucent oil, setting to a hard glass on cooling. Trituration with boiling light petroleum (b.p. 62°-68° C.) gave a crystalline solid. This was recrystallised from methylene chloride/light petroleum (b.p. 40°-60° C.) to give 2-(2',4'-difluoro-2-hydroxy-4-biphenylyl)propan-1-ol, m.p. 118°-118.5° C.

EXAMPLE 9

A solution of 2-(2',4'-difluoro-2-hydroxy-4-biphenylyl)propionic acid (1.75 g.) and thionyl chloride (1 ml.) in dry benzene (10 ml.) was refluxed for 1 hour and then cooled and added dropwise to stirred cold ammonia ($d=0.880$ g./ml; 20 ml.). The product was filtered and recrystallised first from aqueous industrial methylated spirits and then light petroleum (b.p. 62°-68° C.) to give 2-(2',4'-difluoro-2-hydroxy-4-biphenylyl)propionamide, m.p. 222°-224° C.

EXAMPLE 10

A solution of 2-(2',4'-difluoro-2-hydroxy-4-biphenylyl) propionic acid (1 g.) and 2-amino-2-methylpropan-1-ol (1 ml.) in xylene (20 ml.) was stirred under reflux for 3 days. The solvent was distilled and the solid residue was recrystallised from aqueous methanol to give 2-[1-(2',4'-difluoro-2-hydroxy-4-biphenylyl)ethyl]-4,4-dimethyl-2-oxazoline, m.p. 188°-194° C. (decomposes).

EXAMPLE 11

By methods analogous to those described in Example 1, 4-acetyl-2-amino-2'-chloro-4'-fluorobiphenyl was converted to the novel intermediate 4-acetyl-2'-chloro-4'-fluoro-2-methoxy biphenyl, m.p. 81.5°-83.5° C. This was converted to crude 2-(2'-chloro-4'-fluoro-2-methoxy-4-biphenylyl)propionaldehyde and thence to the novel intermediate 2-(2'-chloro-4'-fluoro-2-methoxy-4-biphenylyl)propionic acid, m.p. 138°-140° C.

This was then converted to 2-(2'-chloro-4'-fluoro-2-hydroxy-4-biphenylyl)propionic acid, m.p. 155°-157.5° C., by reaction with hydrobromic acid, in acetic acid.

EXAMPLE 12

By methods analogous to those described in Example 1, 4-acetyl-2-amino-4'-chloro-2'-fluorobiphenyl was converted to the novel intermediate 4-acetyl-4'-chloro-2'-fluoro-2-methoxy-biphenyl, m.p. 81.5°-82.5° C. This was converted to crude 2-(4'-chloro-2'-fluoro-2-methoxy-4-biphenylyl)propionaldehyde and thence to the novel intermediate 2-(4'-chloro-2'-fluoro-2-methoxy-4-biphenylyl)propionic acid, m.p. 135°-137.5° C.

This was then treated with hydrobromic acid in acetic acid to give 2-(4'-chloro-2'-fluoro-2-hydroxy-4-biphenylyl)propionic acid, m.p. 145°-149° C.

EXAMPLE 13

4-Acetyl-2-amino-2'-fluorobiphenyl was diazotised with sodium nitrite. The diazonium compound was refluxed with sulphuric acid for half an hour and then poured into ice-water. The precipitate was extracted in ether, then aqueous sodium hydroxide. This was acidified, to give a brown solid which was washed with water, dried and treated with light petroleum (b.p. 80°-100° C.) in a Soxhlet apparatus. The brown residue which remained was crude 4-acetyl-2'-fluoro-2-hydroxybiphenyl. This was methylated in a similar manner to that described in Example 1 to give almost pure 4-acetyl-2'-fluoro-2-methoxy-biphenyl m.p. 84°-85° C. (after recrystallisation from light petroleum (b.p. 62°-68° C.). This was converted to crude 2-(2'-fluoro-2-methoxy-4-biphenylyl)propionaldehyde and thence to the novel intermediate 2-(2'-fluoro-2-methoxy-4-biphenylyl)propionic acid m.p. 125°-126° C. which on treatment with hydrobromic acid in acetic acid as described in Example 1, gave 2-(2'-fluoro-2-hydroxy-4-biphenylyl)propionic acid, m.p. 110°-111° C.

EXAMPLE 14

2-(2-hydroxy-4-biphenylyl)propionic acid was mixed with an equivalent amount of aqueous sodium hydroxide. The mixture was evaporated to dryness to give sodium 2-(2-hydroxy-4-biphenylyl)propionate, 230 (decomposed)° C.

EXAMPLE 15

2-(2-hydroxy-4-biphenylyl)propionic acid (140 mg.) in ether (5 ml.) was mixed with benzylamine (62 g.) in ether (5 ml.). The precipitate was collected, washed with ether, dried in vacuo and recrystallised for absolute alcohol/ether to give benzylammonium 2-(2-hydroxy-4-biphenylyl)propionate, m.p. 183°-185° C.

EXAMPLE 16

The following mixture was formed into tablets in a conventional manner, each tablet containing 10 mg. of active ingredient.

| | parts |
|---|---|
| 2-(2-hydroxy-4-biphenylyl)propionic | |

| | parts |
|---|---|
| acid | 10 |
| maize starch | 30 |
| lactose | 158 |
| stearic acid | 1 |
| magnesium stearate | 1 |

Similar tablets are prepared containing as the active ingredient the substituted hydroxy propionic acids and their derivatives of Examples 1, 2, 4 and 6 to 15.

It will be understood that the compounds employed in the novel therapeutic compositions and methods of this invention are encompassed by the general formula I of Ser. No. 367,614, the disclosure of which is included herein by reference:

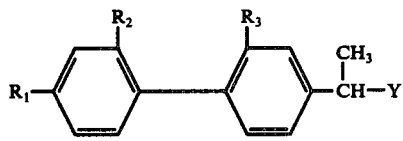

wherein $R_1$, $R_2$ and $R_3$ are individually selected from hydrogen, halogen and hydroxy, provided that at least one of $R_1$, $R_2$ and $R_3$ is hydroxy, and Y is COOH, $CONH_2$, $CH_2OH$, CONHOH or

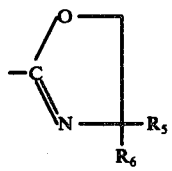

wherein $R_5$ and $R_6$ are the same or different alkyl or hydroxyalkyl, together with pharmaceutically acceptable esters (i.e. compounds wherein Y is $COOR_4$ in which $R_4$ is an esterifying radical) and pharmaceutically acceptable salts of those compounds wherein Y is COOH or CONHOH. More specifically, in this invention $R_1$ and $R_2$ are selected from the group consisting of hydrogen and halogen whereas $R_3$ is hydroxy.

We claim:

1. A therapeutic composition useful in the treatment of pain, inflammation or pyretic conditions or in preventing or inhibiting aggregation of blood platelets which comprises, as active ingredients, a compound of formula I

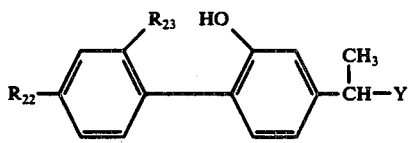

wherein $R_{22}$ and $R_{23}$ are selected from hydrogen and halogen and Y is COOH,
or a pharmaceutically acceptable ester or a salt of a compound wherein Y is COOH and a pharmaceutically acceptable carrier.

2. A composition according to claim 1 in which the halogen of the active ingredient is fluorine or chlorine.

3. A composition according to claim 1 in which the active ingredient is the free acid.

4. A composition according to claim 1 in which the active ingredient is 2-(2-hydroxy-4-biphenylyl)propionic acid.

5. A composition according to claim 1 in which the active ingredient is 2-(4'-chloro-2-hydroxy-4-biphenylyl)propionic acid.

6. A composition according to claim 1 comprising 1 to 1,000 mg. of active ingredient per unit.

7. A composition according to claim 1 in which the active ingredient is 2-(2'-fluoro-2-hydroxy-4-biphenylyl)propionic acid.

8. A method of treating inflammation in a patient requiring treatment therefor which comprises administering to said patient an effective amount of a compound of formula I

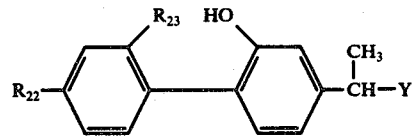

wherein $R_{22}$ and $R_{23}$ are selected from hydrogen and halogen and Y is COOH,
or a pharmaceutically acceptable ester or a salt of a compound wherein Y is COOH.

9. A method according to claim 8 which comprises administering 0.03 to 60 mg. of the compound per kg. of the body weight of the patient per day.

10. A method according to claim 8 wherein said compound is 2-(2-hydroxy-4-biphenylyl)propionic acid.

11. A method according to claim 8 wherein said compound is 2-(2'-fluoro-2-hydroxy-4-biphenylyl) propionic acid.

12. A method of treating pain in a patient requiring treatment therefor which comprises administering to said patient an effective amount of a compound of formula I

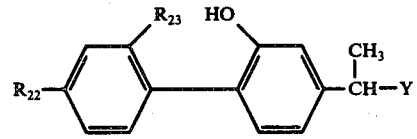

wherein $R_{22}$ and $R_{23}$ are selected from hydrogen and halogen and Y is COOH, or a pharmaceutically acceptable ester or a salt of a compound wherein Y is COOH.

13. A method according to claim 12 which comprises administering 0.03 to 60 mg. of the compound per kg. of the body weight of the patient per day.

14. A method according to claim 12 wherein said compound is 2-(2-hydroxy-4-biphenylyl) propionic acid.

15. A method according to claim 12 wherein said compound is 2-(2'-fluoro-2-hydroxy-4-biphenylyl) propionic acid.

16. A method of treating pyretic conditions in a patient requiring treatment therefor which comprises administering to said patient an effective amount of a compound of formula I

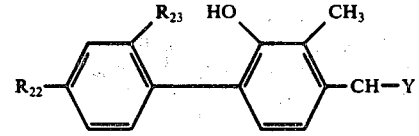

wherein $R_{22}$ and $R_{23}$ are selected from hydrogen and halogen and Y is COOH, or a pharmaceutically acceptable ester or a salt of a compound wherein Y is COOH.

17. A method according to claim 16 which comprises administering 0.03 to 60 mg. of the compound per kg. of the body weight of the patient per day.

18. A method according to claim 16 wherein said compound is 2-(2-hydroxy-4-biphenylyl) propionic acid.

19. A method according to claim 16 wherein said compound is 2-(2'-fluoro-2-hydroxy-4-biphenylyl) propionic acid.

20. A method of preventing or inhibiting aggregation of blood platelets in a patient requiring treatment therefor which comprises administering to said patient an effective amount of a compound of formual I

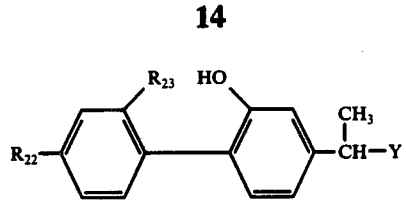

wherein $R_{22}$ and $R_{23}$ are selected from hydrogen and halogen and Y is COOH, or a pharmaceutically acceptable ester or a salt of a compound wherein Y is COOH.

21. A method according to claim 20 which comprises administering 0.03 to 60 mg. of the compound per kg. of the body weight of the patient per day.

22. A method according to claim 20 wherein said compound is 2-(2-hydroxy-4-biphenylyl) propionic acid.

23. A method according to claim 20 wherein said compound is 2-(2'-fluoro-2-hydroxy-4-biphenylyl) propionic acid.

* * * * *